United States Patent [19]

Nadland et al.

[11] Patent Number: 4,959,222

[45] Date of Patent: Sep. 25, 1990

[54] MAGNESIUM ADDITIVE FOR NUTRIENTS, FEED, AND MEDICAMENTS

[75] Inventors: Karl J. Nadland, Lier; Mari A. Kleppe, Tranby, both of Norway

[73] Assignee: Collett-Marwell Hauge A/S, Asker, Norway

[21] Appl. No.: 248,419

[22] Filed: Sep. 23, 1988

[30] Foreign Application Priority Data

Sep. 28, 1987 [NO] Norway ................................. 874067

[51] Int. Cl.$^5$ ..................... A61K 33/08; A61K 33/06; A61K 31/19
[52] U.S. Cl. .................................. 424/692; 424/688; 424/682; 514/574
[58] Field of Search ............... 424/154, 682, 692, 688; 514/574

[56] References Cited

U.S. PATENT DOCUMENTS

| | | | |
|---|---|---|---|
| 2,816,854 | 12/1957 | Gross | 424/143 |
| 4,202,887 | 5/1980 | Talbot et al. | 424/154 |
| 4,619,829 | 10/1986 | Motschan | 424/128 |

*Primary Examiner*—Douglas W. Robinson
*Assistant Examiner*—Raymond J. Henley, III
*Attorney, Agent, or Firm*—Fleit. Jacobson, Cohn, Price, Holman & Stern

[57] ABSTRACT

A mineral additive to be added to nutrients, feed, and medicaments, and which comprises a source of magnesium is characterized by comprising:
(1) magnesium lactate;
(2) water soluble, acidic, substantially dibasic magnesium citrate; and if desired
(3) magnesium hydroxide; and, if desired additionally
(4) a carbohydrate additive.

The quantity of magnesium citrate preferably constitutes 5 to 15% by weight, calculated as magnesium.

11 Claims, No Drawings

MAGNESIUM ADDITIVE FOR NUTRIENTS, FEED, AND MEDICAMENTS

The present invention relates to a mineral additive to be added to nutrients, feed, and medicaments.

Clinical medicine in recent years experienced an increasing tendency to observe the influence of elemental magnesium.

This, in turn, caused an intensified research in this field.

In the intercellular liquid system magnesium is one of the most important minerals and a grown up person weighing approximately 70 kg has approximately 20 g magnesium in his body of which approximately 50-60% are found in bone substance and the rest in muscles (skelton musculature, heart, etc.) and in soft tissue.

Available literature indicates that magnesium acts as an activator of at least 300 different enzyme systems in the animal body. The influence of magnesium is, among others, important for activation of the enzymes controlling conversion of carbohydrates, fat, and electrolytes. Cell permeability and neuromuscular irritability, as well as division and transfer of phosphate groups are all functions dependent on elemental magnesium.

This mineral also influences the ATPase-metabolism and, thus, influences muscle contraction, glucose utilizing protein-, nucleic acid, and fatty acid syntheses.

Efforts were made lately to survey the influence of a deficiency of magnesium on a series of clinical conditions, but verification proved to be difficult.

However, the following clinical picture seems to be present:
1. Disturbance of the central nervous system with apathy, depression, lack of appetite, disorientation, and coma;
2. disturbance of the skeleton muscle system with muscle twitches, cramps, ataxy, muscular weakness;
3. disease of the heart and blood vessels, i.e. arythmia, ischemia, hypertension, and acute cardiac arrest;
4. gastrointestinal fenomena, like anorexia, diffuse abdominal pains, diarrhoea and obstipation.

Based on the theory that certain of these phenomena may be due to magnesium failure, experiments were made with magnesium additives.

Magnesium in the form of various salts is generally a difficult mineral for administration, since it provokes a bitter/sour taste which is generally not organoleptically acceptable.

It was, thus, an object of the present invention to find the best possible magnesium compound or mixture of such compounds for use in an organoleptically acceptable preparation.

This object was achieved by a mineral additive to be added to nutrients, feed, and medicaments, and said additive is characterized by comprising:
1. magnesium lactate;
2. water soluble, acidic, substantially diabasic magnesium citrate; if desired
3. magnesium hydroxide; and, if desired, additionally
4. a carbon hydrate additive.

Whereas previous efforts (see list of references) were not very successful as regards providing organoleptically acceptable magnesium additives, it was surprisingly found that the combination according to the invention provides an organoleptically acceptable and organically absorbable magnesium salt mixture. By combining magnesium lactate and a magnesium citrate, as mentioned, it is possible to provide a neutral and acceptable additive without any subflavour or aftertaste. This is achieved in spite of the fact that the results are much less attractive when each of these compounds is used alone. Whereas, e.g. an additive produced on the basis of magnesium lactate has a bitter taste, and a tablet on the basis of said magnesium citrate alone is too sour, both substances in combination will provide an organoleptically acceptable additive. It is known from literature that said magnesium compounds per se are used in commercial magnesium tablets, but the combination according to the invention is new and proved to have very surprising positive results.

The combination of lactate and citrate according to the invention may be varied within relatively wide areas, also with more sweetener in case of a larger content of such a citrate.

A preferred embodiment has a content of citrate between 5 and 15% of the total magnesium compounds, calculated as magnesium. It may be advantageous to add the carbohydrate as a carrier, however, this is solely done for production technical reasons.

In a possible variant part of the magnesium may be added in the form of magnesium hydroxide with a combination of magnesium lactate and the water soluble citrate. This is advantageous since the composition of raw materials is slightly less expensive.

The invention is illustrated by the following examples 1-10, however, the following should be mentioned at first:

A series of the above mentioned inorganic salts were previously used, and are obviously well known in the Art.

Examples of such salts are:
1. Magnesium chloride which is a bitter salt, but much used. Solutions of magnesium chloride are at present mostly used in connection with haemodialysis and peritoneal dialysis;
2. basic magnesium carbonate which is a combination of magnesium carbonate and magnesium hydroxide, best known in the Art as antacid and often used with aluminium hydroxide; the compound has a relatively neutral flavor and odour, but it may cause diarrhoea and irritation of the mucous membrane of the stomach;
3. magnesium hydroxide (per se) is also a relatively neutral salt as regards odour and flavor, but in a relatively pure state and high concentration it will have a slightly nauseous flavor, the salt is mostly used as antacid and may have a weak purging effect when taken in large doses; magnesium oxide has a slightly alkaline and also nauseous flavor, this salt is mostly known and used as antasid and is also a mild laxative;
4. magnesium sulphate is a well known salt which is disclosed in many pharmacopoeia; the salt is very hygroscopic and has a cooling, salty and bitter flavor, the salt is mostly used in the form of a solution;
5. magnesium phosphate is relatively neutral in the same manner as magnesium oxide and magnesium hydroxide and is used as antracid and is a mild laxative.

The other main group of magnesium compounds comprises organic compounds which, obviously, have a much lower content of magnesium and generally show less inconvenient physiological side effects than most of the inorganic salts.

Some of these salts are mentioned below:

Magnesium lactate is a slightly water soluble compound which has a slightly bitter taste even in a well purified state.

Magnesium gluconate is relatively neutral, but in a processed state with carbohydrates it will leave a slightly bitter after-taste, and it tends slightly to stick to the teeth.

Trimagnesium citrate is a not very water soluble salt leaving a bitter taste in a dry state, also there is an exothermic heat generation when water is added, which is most disagreable when taken orally.

Water soluble, acidic, substantially dibasic magnesium citrate is a slightly more soluble salt but with a quite acidic taste.

Magnesium orotate is difficultly soluble in water and has a disagreable metal taste (after-taste).

Magnesium aspartate is easily soluble, but regrettably, has an unattractive metalic taste. It is reported that the compound causes diarrhoea when taken in large quantities.

As mentioned above, it was now found that it is possible to combine certain magnesium salts which would each, taken per se, cause organoleptical discomfort or undesired side effects, but which in a combination according to the invention permit administration of the necessary elemental magnesium to the organism without causing unacceptable organoleptic properties.

Among literature we refer to the following in this connection:
1. Martindale "The Extra Pharmacopoeia", Twenty-eighth Edition, James E. F. Reynolds.
2. 1983, Year Book Medical Publishers Inc., "Magnesium Deficiency", p. 509–533, Robert E. Cronin, M.D. and James P. Knochel RD.
3. "Magnesium og hjerte- og karsykdommer", Tidsskr. Nor. Læ geforen. No. 7, 1986, 106. 554–7, Lars Gullestad, Einar Søyland, John Kjekshus, Med. Dep. Bæ rum Sykehus.
4. Medicinsk Årbog, 1984, Munksgaard, Copenhagen. "Magnesiumbrist—et nytt syndrom", p. 53–66. Thomas Dyckner and Per Olav Wester.
5. "The Merck Index", Merck et Co. Inc. N.J.U.S.A., 1976, p. 736–739.

The following examples will illustrate possible formulations without limiting the invention to them.

EXAMPLES

95–120 mg $Mg^{2+}$ per tablet (1) The following ingredients were granulated in a high-speed mixer:

| Mg lactate | 4430 g |
| --- | --- |
| sorbitol | 1024 g |
| granulating liquid | 560 g |
| total | 5914 g |

The granulate was dried in a cabinet dryer for 12 hours at 55° C.

The dried granulate was granulated on a 12 mesh cloth and was mixed with the following ingredients:

| granulate | 548 g |
| --- | --- |
| 4% flavor conc. | 16 g |
| citric acid | 4 g |
| aspartame | 1 g |
| Mg stearate | 5 g |

The mixture was pelleted by 16 mm tools. Taste when chewed: bitter.

(2) (a) Granulate

| water soluble, acidic substantially dibasic Mg citrate | 4500 g |
| --- | --- |
| sugar | 1000 g |
| granulating liquid | 550 g |
| total | 6050 g |

The granulate was manufactured according to the same procedure as disclosed in Example 1.

(b) Tablets

| granulate | 540 g |
| --- | --- |
| 4% flavor conc. | 22 g |
| aspartame | 2,0 g |
| Mg stearate | 5.1 g |

Tablets manufactured with a diameter of 16 mm. Taste strongly acidic.

(3) Method as disclosed in Example 1.
Combination of Mg lactate/Mg citrate (dibasic)
(a) Granulate

| Mg lactate | 2954 g |
| --- | --- |
| water soluble, acidic substantially dibasic Mg citrate | 1750 g |
| granulating liquid | 520 g |
| total | 5224 g |

The granulate was dried for 24 hours at 55°C.

(b) Tablets

| granulate | 460 g |
| --- | --- |
| 4% flavor conc. | 16 g |
| apartame | 2 g |
| Mg stearate | 4.9 g |

16 mm tablets. Taste: relatively agreeable, but slightly too acidic.

(4) (a) Granulate

| Mg lactate | 3690 g |
| --- | --- |
| water soluble, acidic substantially dibasic Mg citrate | 875 g |
| granulating liquid | 500 g |
| total | 5065 g |

(b) Tablets

| granulate | 450 g |
| --- | --- |
| 4% flavor conc. | 16 g |
| aspartame | 1 g |
| Mg stearate | 4.9 g |

16 mm tablets. Taste: better than Example 3, slightly less acidic.

Manufacture as in Examples 3 and 1.
(5) (a) Granulate

| Mg lactate | 4060 g |
| --- | --- |

-continued

|  |  |
|---|---|
| Mg citrate, water soluble, acidic substantially dibasic Mg citrate | 440 g |
| granulating liquid | 490 g |
| total | 4990 g |

(b) Tablets

|  |  |
|---|---|
| granulate | 440 g |
| 4% flavor conc. | 16 g |
| aspartame | 1 g |
| Mg stearate | 4.9 g |

16 mm tablets. Taste: Agreeable, refreshing.

(6) (a) Granulate

|  |  |
|---|---|
| Mg lactate | 4245 g |
| Mg citrate, water soluble, acidic substantially dibasic Mg citrate | 220 g |
| granulating liquid | 490 g |
| total | 4955 g |

(b) Tablets

|  |  |
|---|---|
| granulate | 440 g |
| 4% flavor conc. | 16 g |
| aspartame | 1 g |
| Mg stearate | 4.9 g |

Manufacture as in Examples 1 and 3. 16 mm tablets. Taste: agreeable, relatively neutral, slightly acidulous (no subflavor).

(7) (a) Granulate

|  |  |
|---|---|
| Mg lactate | 3380 g |
| water soluble, acidic substantially dibasic Mg citrate | 364 g |
| Mg hydroxide | 250 g |
| granulating liquid | 450 g |
| total | 4444 g |

(b) Tablets

|  |  |
|---|---|
| granulate | 390 g |
| 4% flavor conc. | 16 g |
| aspartame | 1 g |
| Mg stearate | 4.8 g |

Manufacture as in Example 1. 16 mm tablets. Taste: Agreeable, neutral, refreshing (a weak subflavor/aftertaste?).

(3) Variation of the hydrate quantity
(a) Granulate

|  |  |
|---|---|
| Mg lactate | 2950 g |
| water soluble, acid substantially dibasic Mg citrate | 855 g |
| Sorbitol | 575 g |
| granulating liquid | 425 g |
| total | 4705 g |

The granulate is dried for 25 hours at 55° C. on a tray.

(b) Tablets

|  |  |
|---|---|
| granulate | 455 g |
| 4% flavor conc. | 17 g |
| aspartame | 1 g |
| Mg stearate | 4.9 g |

16 mm tablets. Taste good agreeable.

(9) (a) Granulate

|  |  |
|---|---|
| Mg lactate | 2950 g |
| water soluble, acidic substantially dibasic Mg citrate | 855 g |
| Sugar | 1850 g |
| granulating liquid | 480 g |
| total | 6135 g |

(b) Tablets

|  |  |
|---|---|
| granulate | 550 g |
| 4% flavor conc. | 19 g |
| aspartame | 1 g |
| Mg stearate | 5.0 g |

16 mm tablets. Taste sweet, taste good.

(10) (a) Granulate

|  |  |
|---|---|
| Mg lactate | 2959 g |
| water soluble, acidic substantially dibasic Mg citrate | 855 g |
| Xylitol | 590 g |
| granulating liquid | 425 g |
| total | 4820 g |

(b) Tablets

|  |  |
|---|---|
| granulate | 455 g |
| 4% flavor conc. | 17 g |
| aspartame | 1 g |
| Mg stearate | 4.9 g |

16 mm tablets. Taste: Sweetish, refreshing, neutral.

In the above Examples a granulate was manufactured and converted into tablets to simplify comparison.

Those skilled in the art will obviously understand that other conventional forms of administration may be utilized.

We claim:

1. An organoleptically acceptable mineral granulate for human consumption in medicaments or as a food additive that consists essentially of a granulating liquid and a mixture of magnesium salts, wherein said mixture contains magnesium lactate and water soluble, acidic, substantially dibasic magnesium citrate, wherein the amount of the magnesium citrate equals from 1 to 40% by weight of the total magnesium in said granulate, the amount of said liquid is sufficient to form said granulate, and the amount of magnesium lactate and dibasic magnesium citrate in said granulate are sufficient to render compositions to which said granulate is added organoleptically acceptable.

2. The mineral granulate of claim 1 wherein said mixture of magnesium salts also includes magnesium hydroxide which constitutes up to 50% by weight of the total magnesium in said granulate.

3. The mineral granulate of claim 1, wherein said mixture of magnesium salts also includes magnesium hydroxide which constitutes from 10 to 30% by weight of the total magnesium in said granulate.

4. The mineral granulate of claim 1, wherein said amount of the magnesium citrate is from 5 to 15% by weight.

5. The mineral granulate of claim 4, wherein said mixture of magnesium salts also includes magnesium hydroxide which constitutes up to 50% by weight of the total magnesium in said mineral granulate.

6. The mineral granulate of claim 4, wherein said mixture of magnesium salts also includes magnesium hydroxide which constitutes from 10 to 30% by weight of the total magnesium in said mineral granulate.

7. An organoleptically acceptable mineral granulate for human consumption in medicaments or as a food additive that consists essentially of a granulating liquid, a carbohydrate additive, and a mixture of magnesium salts, wherein said mixture contains magnesium lactate and water soluble, acidic, substantially dibasic magnesium citrate, wherein the amount of magnesium citrate equals from 1 to 40% by weight of the total magnesium in said granulate, the amount of said liquid is sufficient to form said granulate, and the amount of magnesium lactate and dibasic magnesium citrate in said granulate are sufficient to render compositions to which said granulate is added organoleptically acceptable.

8. The mineral granulate of claim 7, wherein said amount of magnesium citrate is from 5 to 15% by weight.

9. The mineral granulate of claim 7, wherein said mixture of magnesium salts also includes magnesium hydroxide which constitutes up to 50% by weight of the total magnesium in said granulate.

10. The mineral granulate of claim 9, wherein said amount of magnesium citrate is from 5 to 15% by weight.

11. The mineral granulate of claim 7, wherein said mixture of magnesium salts also includes magnesium hydroxide which constitutes from 10 to 30% by weight of the total magnesium in said granulate.

* * * * *